(12) United States Patent
Lenker et al.

(10) Patent No.: US 11,986,202 B2
(45) Date of Patent: May 21, 2024

(54) STEERABLE ENDOLUMINAL PUNCH WITH INTRODUCER AND GUIDEWIRE

(71) Applicant: Indian Wells Medical, Inc., Lake Forest, CA (US)

(72) Inventors: Jay Alan Lenker, Lake Forest, CA (US); James Alexander Carroll, Long Beach, CA (US); Eugene Michael Breznock, Winters, CA (US); Donald J. Kolehmainen, Laguna Niguel, CA (US); Peter van der Sluis, Scottsdale, AZ (US)

(73) Assignee: Indian Wells Medical, Inc., Lake Forest, CA (US)

( * ) Notice: Subject to any disclaimer, the term of this patent is extended or adjusted under 35 U.S.C. 154(b) by 0 days.

(21) Appl. No.: 18/314,462

(22) Filed: May 9, 2023

(65) Prior Publication Data
US 2023/0277208 A1  Sep. 7, 2023

Related U.S. Application Data

(63) Continuation of application No. 17/878,552, filed on Aug. 1, 2022, now Pat. No. 11,648,025.
(Continued)

(51) Int. Cl.
*A61B 17/32* (2006.01)
*A61B 17/00* (2006.01)
*A61B 17/3205* (2006.01)

(52) U.S. Cl.
CPC ........... *A61B 17/320016* (2013.01); *A61B 17/32053* (2013.01); *A61B 2017/00247* (2013.01); *A61B 2017/320052* (2013.01)

(58) Field of Classification Search
CPC ........... A61B 2017/00247; A61B 2017/00252; A61B 2017/320052; A61B 17/320016; A61B 17/32053
See application file for complete search history.

(56) References Cited

U.S. PATENT DOCUMENTS

| 3,802,440 A | 4/1974 | Salem |
| 4,757,827 A | 7/1988 | Buchbinder et al. |

(Continued)

FOREIGN PATENT DOCUMENTS

| EP | 1898801 | 3/2008 |
| JP | 2004508147 | 3/2004 |

(Continued)

OTHER PUBLICATIONS

Examiner's Report and Examination Search Report from Canadian Patent Application No. 2,870,854 dated Nov. 7, 2019.
(Continued)

*Primary Examiner* — Wade Miles
(74) *Attorney, Agent, or Firm* — Crockett & Crockett, PC; K. David Crockett, Esq.

(57) ABSTRACT

An endoluminal punch and introducer sheath are described wherein the endoluminal punch comprises a guidewire lumen through which a user is capable of placing a guidewire. The endoluminal punch system further comprises a mechanism affixed to the hub which is capable of controlling the axial positioning of the guidewire relative to the endoluminal punch distal end. The control mechanism can be released so that the endoluminal punch can be removed from a patient while retaining the guidewire in place within the patient. The endoluminal punch introducer, including a sheath and dilator, can comprise energy emitting electrodes or transducers for cutting larger size holes in stubborn (friable, scarred, or fibrotic) tissue. In other embodiments, the endoluminal punch can comprise a guidewire or stylet, (Continued)

wherein the guidewire or stylet is capable of emitting energy to cut through tissue.

3 Claims, 12 Drawing Sheets

Related U.S. Application Data

(60) Provisional application No. 63/340,846, filed on May 11, 2022, provisional application No. 63/329,302, filed on Apr. 8, 2022, provisional application No. 63/227,835, filed on Jul. 30, 2021.

(56) References Cited

U.S. PATENT DOCUMENTS

| | | | |
|---|---|---|---|
| 4,815,478 | A | 3/1989 | Buchbinder et al. |
| 5,725,512 | A | 3/1998 | Swartz et al. |
| 6,136,016 | A | 10/2000 | Barbut et al. |
| 6,217,527 | B1 | 4/2001 | Selmon et al. |
| 6,419,641 | B1 | 7/2002 | Mark et al. |
| 6,650,923 | B1 | 11/2003 | Lesh |
| 6,695,814 | B2 | 2/2004 | Greene et al. |
| 7,471,697 | B2 | 12/2008 | Kamiya |
| 7,488,448 | B2 | 2/2009 | Wieting et al. |
| 7,615,044 | B2 | 11/2009 | Scheibe |
| 7,632,277 | B2 | 12/2009 | Woll |
| 7,678,081 | B2 | 3/2010 | Whiting et al. |
| 7,824,356 | B2 | 11/2010 | Wieting et al. |
| 7,935,102 | B2 | 5/2011 | Breznock et al. |
| 8,235,943 | B2 | 8/2012 | Breznock et al. |
| 8,323,241 | B2 | 12/2012 | Salahieh et al. |
| 8,480,606 | B2 | 7/2013 | Wieting et al. |
| 8,491,619 | B2 | 7/2013 | Breznock |
| 8,939,926 | B2 | 1/2015 | Wieting et al. |
| 8,961,550 | B2 | 2/2015 | Lenker et al. |
| 9,445,836 | B2 | 9/2016 | Breznock |
| 9,555,182 | B2 | 1/2017 | Wieting et al. |
| 9,707,007 | B2 | 7/2017 | Lenker et al. |
| 9,993,266 | B2 | 6/2018 | Lenker et al. |
| 10,016,210 | B2 | 7/2018 | Lenker et al. |
| 10,016,221 | B2 | 7/2018 | Lenker et al. |
| 10,034,686 | B2 | 7/2018 | Breznock |
| 10,369,265 | B2 | 8/2019 | Wieting et al. |
| 10,485,569 | B2 | 11/2019 | Lenker et al. |
| 10,485,579 | B2 | 11/2019 | Lenker |
| 10,729,457 | B2 | 8/2020 | Lenker et al. |
| 10,779,858 | B2 | 9/2020 | Lenker et al. |
| 10,786,655 | B2 | 9/2020 | Lenker |
| 10,806,483 | B2 | 10/2020 | Breznock |
| 10,932,815 | B1 | 3/2021 | Lenker et al. |
| 11,090,080 | B2 | 8/2021 | Lenker et al. |
| 11,234,728 | B2 | 2/2022 | Lenker et al. |
| 11,317,938 | B2 | 5/2022 | Lenker et al. |
| 11,382,654 | B2 | 7/2022 | Lenker |
| 11,490,922 | B2 | 11/2022 | Lenker et al. |
| 2004/0193073 | A1 | 9/2004 | DeMello et al. |
| 2004/0267361 | A1 | 12/2004 | Donnelly et al. |
| 2005/0004515 | A1 | 1/2005 | Hart et al. |
| 2005/0101984 | A1 | 5/2005 | Chanduszko et al. |
| 2005/0267495 | A1 | 12/2005 | Ginn et al. |
| 2006/0074442 | A1 | 4/2006 | Noriega et al. |
| 2006/0252984 | A1* | 11/2006 | Rahdert ............. A61B 17/0401 623/2.37 |
| 2007/0060878 | A1 | 3/2007 | Bonnette et al. |
| 2008/0045863 | A1 | 2/2008 | Bakos |
| 2008/0045908 | A1 | 2/2008 | Gould et al. |
| 2008/0243081 | A1 | 10/2008 | Nance |
| 2009/0036832 | A1 | 2/2009 | Skujins et al. |
| 2010/0185053 | A1 | 7/2010 | Hagen |
| 2010/0228276 | A1 | 9/2010 | Breznock |
| 2011/0245615 | A1 | 10/2011 | Iwasaka et al. |
| 2011/0245800 | A1 | 10/2011 | Kassab et al. |
| 2011/0319905 | A1 | 12/2011 | Palme et al. |
| 2014/0343538 | A1 | 11/2014 | Lenker et al. |
| 2018/0317949 | A1 | 11/2018 | Lenker et al. |
| 2022/0370121 | A1* | 11/2022 | Highsmith ............. A61M 29/00 |

FOREIGN PATENT DOCUMENTS

| | | |
|---|---|---|
| WO | WO9513752 | 5/1995 |
| WO | WO0064525 | 11/2000 |
| WO | WO2007-035497 | 3/2007 |
| WO | WO2007-115314 | 10/2007 |
| WO | WO2008069772 | 6/2008 |
| WO | WO2009112060 | 9/2009 |
| WO | WO2010151698 | 12/2010 |

OTHER PUBLICATIONS

Office Action dated Jul. 19, 2018 from European Patent Application No. 13861154.6.
International Search Report dated Jul. 18, 2013 from PCT Application PCT/US2013/034474.
Search Report dated May 16, 2013 from GB Application GB1308015.5.
International Search Report dated Mar. 6, 2014 from PCT Application PCT/US2013/073262.
Extended European Search Report dated Aug. 4, 2015 from EP Application 13778011.0.
Extended European Search Report dated Jun. 16, 2016 from European Patent Application 13861154.6.
Office Action dated Feb. 23, 2017 from Chinese Patent Application No. 201380072336.2.
Examination Report dated Oct. 6, 2017 from European Patent Application No. 13861154.6.
Notification of Reasons for Refusal dated Oct. 24, 2017 from Japanese Patent Application No. 2015545833.

* cited by examiner

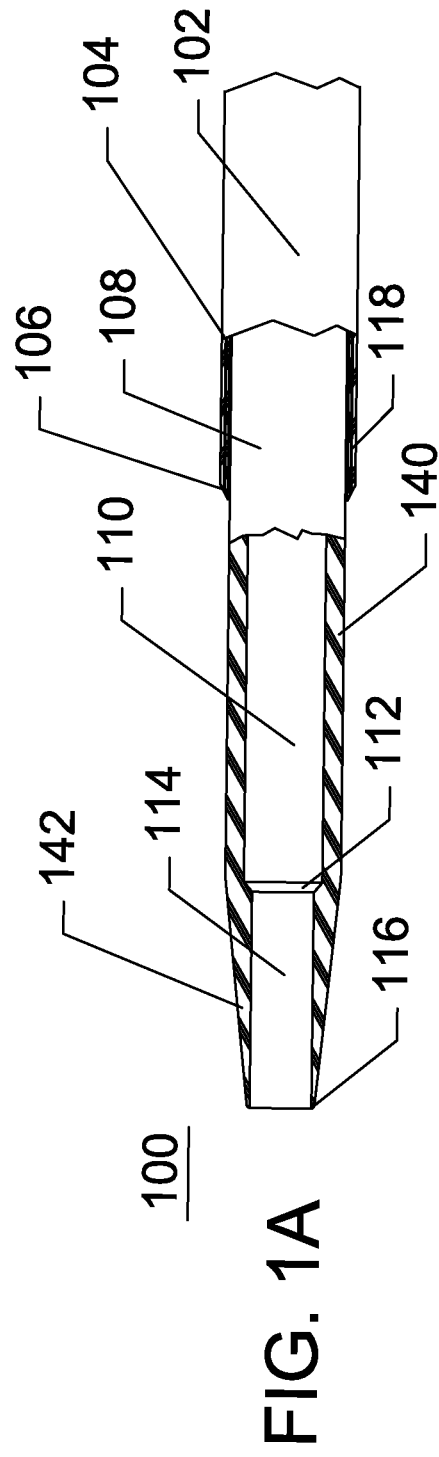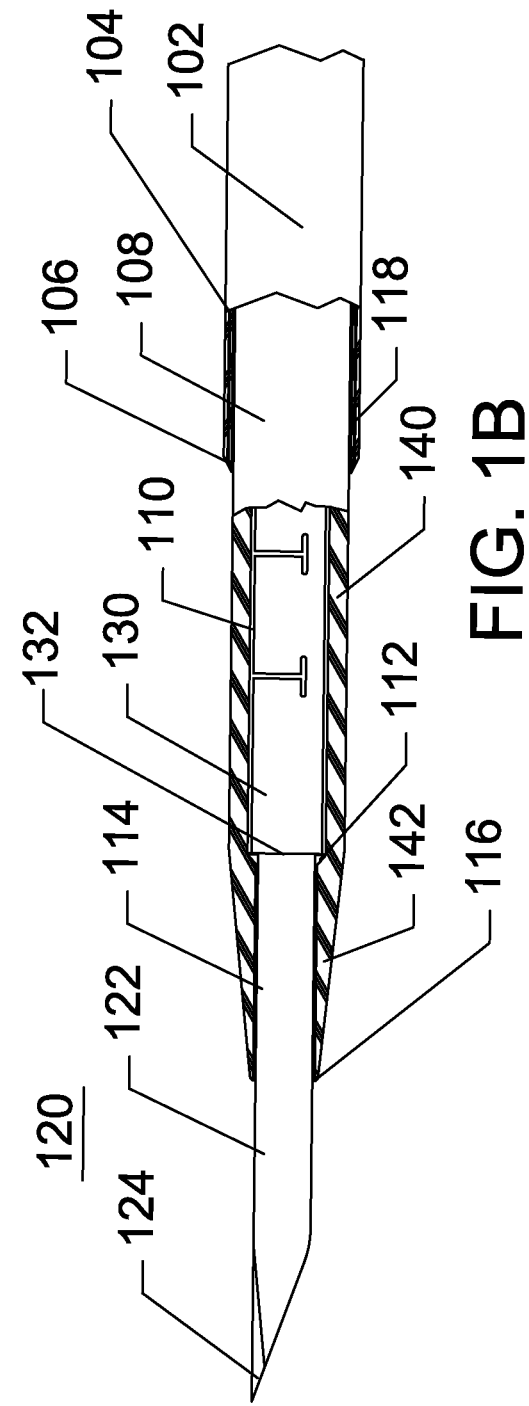

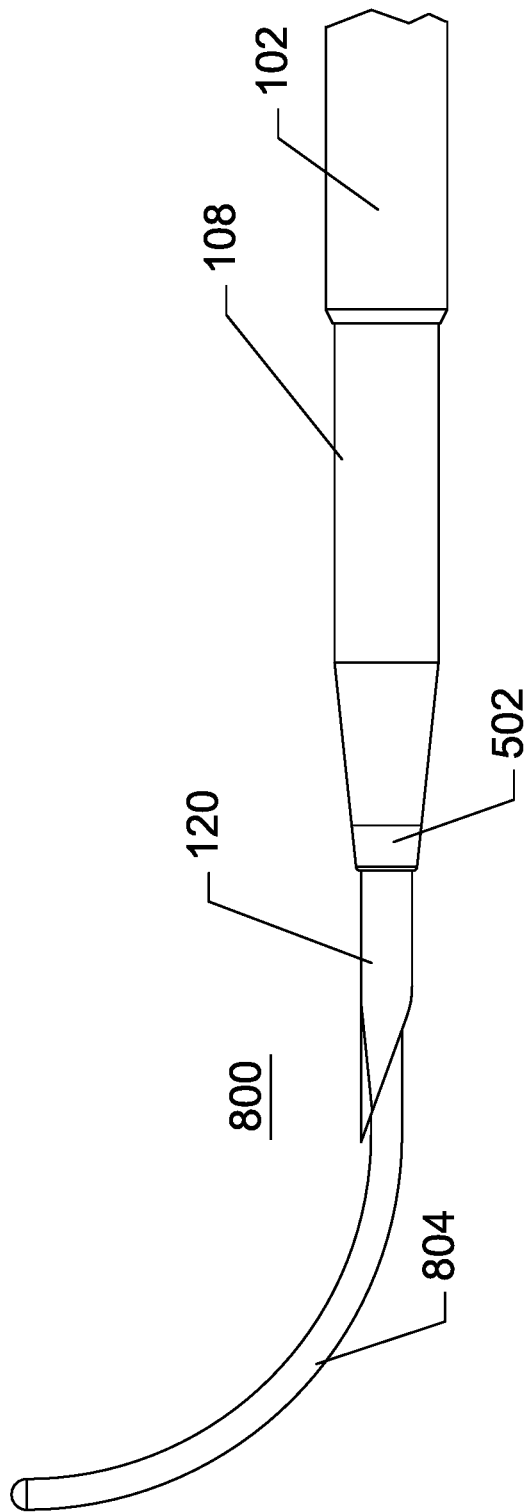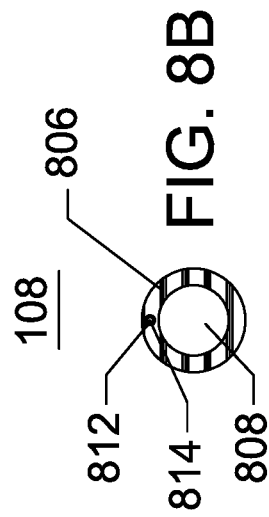

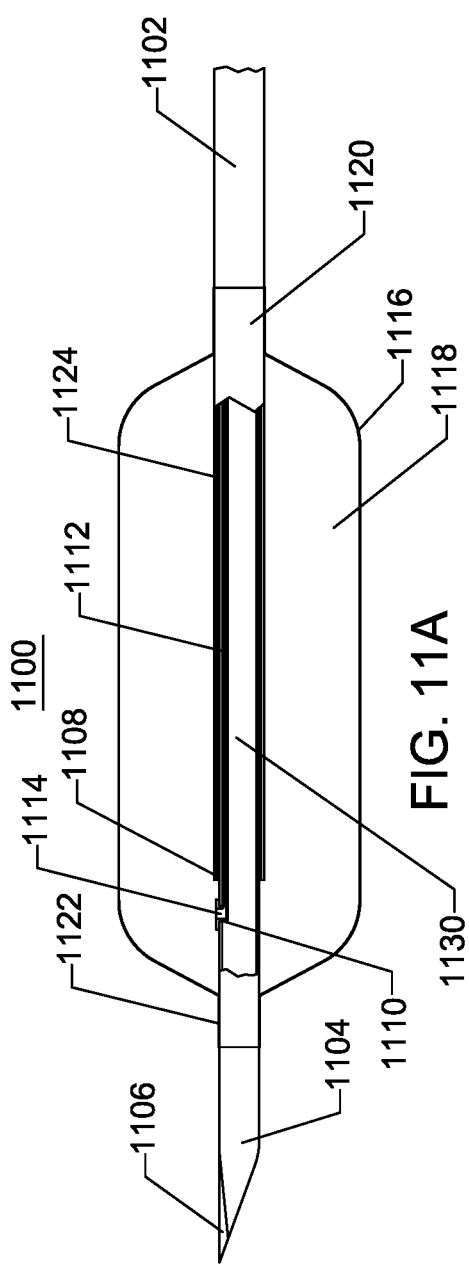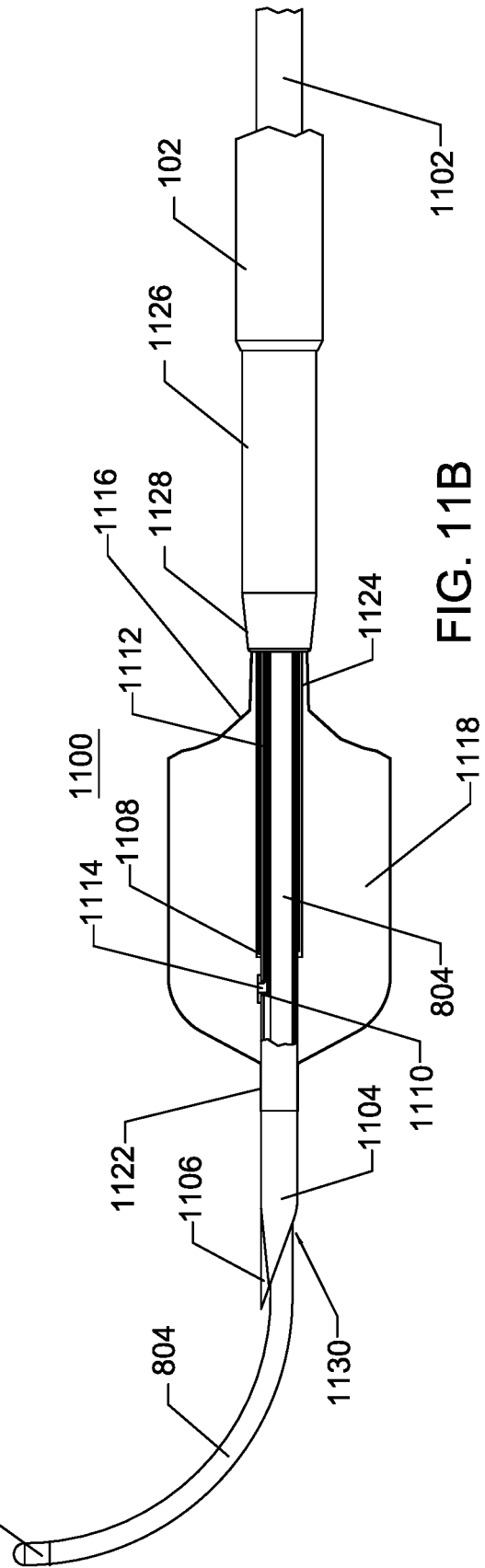

025 US 11,986,202 B2

STEERABLE ENDOLUMINAL PUNCH WITH INTRODUCER AND GUIDEWIRE

This application is a continuation of U.S. application Ser. No. 17/878,552, filed Aug. 1, 2022, now U.S. Pat. No. 11,648,025, which claims priority to U.S. Provisional Application 63/227,835, filed Jul. 30, 2021, U.S. Provisional Application 63/329,302 filed Apr. 8, 2022, and U.S. Provisional Application 63/340,846, filed May 11, 2022.

FIELD OF THE INVENTION

The invention relates to devices and methods for performing endovascular access to the cardiovascular system or other body vessels or body lumens, especially procedures performed in the fields of cardiology, radiology, electrophysiology, and surgery.

BACKGROUND

The currently accepted procedure for left atrial access involves routing a needle called a Brockenbrough needle into the right atrium with the Brockenbrough needle pre-placed within a guiding catheter. The guiding catheter specifically preferred for use with a Brockenbrough needle is called a Mullins-type catheter or transseptal introducer. The Brockenbrough needle is a long, small diameter punch, generally formed from a stainless steel wire stylet that is surrounded by a stainless steel tube. Other devices, designed for the same purpose, employ radiofrequency ablation to perforate the atrial wall but these devices expose the myocardium to burning, potentially reduced healing characteristics, and increased risk of subsequent scarring.

BRIEF DESCRIPTION OF THE DRAWINGS

FIG. 1A illustrates an introducer capable of delivering a steerable endoluminal punch (steerable endoluminal punch), as viewed from the side in cross-section, whereby the dilator and sheath comprise the same outside diameter as standard transseptal introducers, but with a larger diameter lumen within the dilator, according to an embodiment of the invention;

FIG. 1B illustrates the introducer of FIG. 1A further with a large diameter steerable endoluminal punch introduced through the central lumen of the dilator, the steerable endoluminal punch further including a stubby blunt stylet to shield the sharp tip during insertion through the introducer dilator lumen, according to an embodiment of the invention;

FIG. 8A illustrates the steerable endoluminal punch of FIG. 6A wherein the protective stylet, or guidewire, has been actuated and has advanced to a position which is distal to the sharp distal end of the endoluminal punch. The blunt distal end of the protective stylet or guidewire is purposefully oriented to curve in the direction of the sharp tip and provides greater protection for the sharp distal end of the endoluminal punch from inadvertently puncturing unplanned tissue or other structures, according to an embodiment of the invention;

FIG. 8B illustrates a longitudinal cross-sectional view of the dilator which includes a central lumen and an electrical bus, according to an embodiment of the invention;

FIG. 11A illustrates a steerable endoluminal punch further comprising a dilatation balloon affixed thereto and operably inflated/deflated through a channel in the steerable endoluminal punch, according to an embodiment of the invention;

FIG. 11B illustrates the steerable endoluminal punch of FIG. 11A wherein the dilatation balloon is being deflated and withdrawn back into the dilator lumen of an introducer, according to an embodiment of the invention;

DETAILED DESCRIPTION

Figure 2:
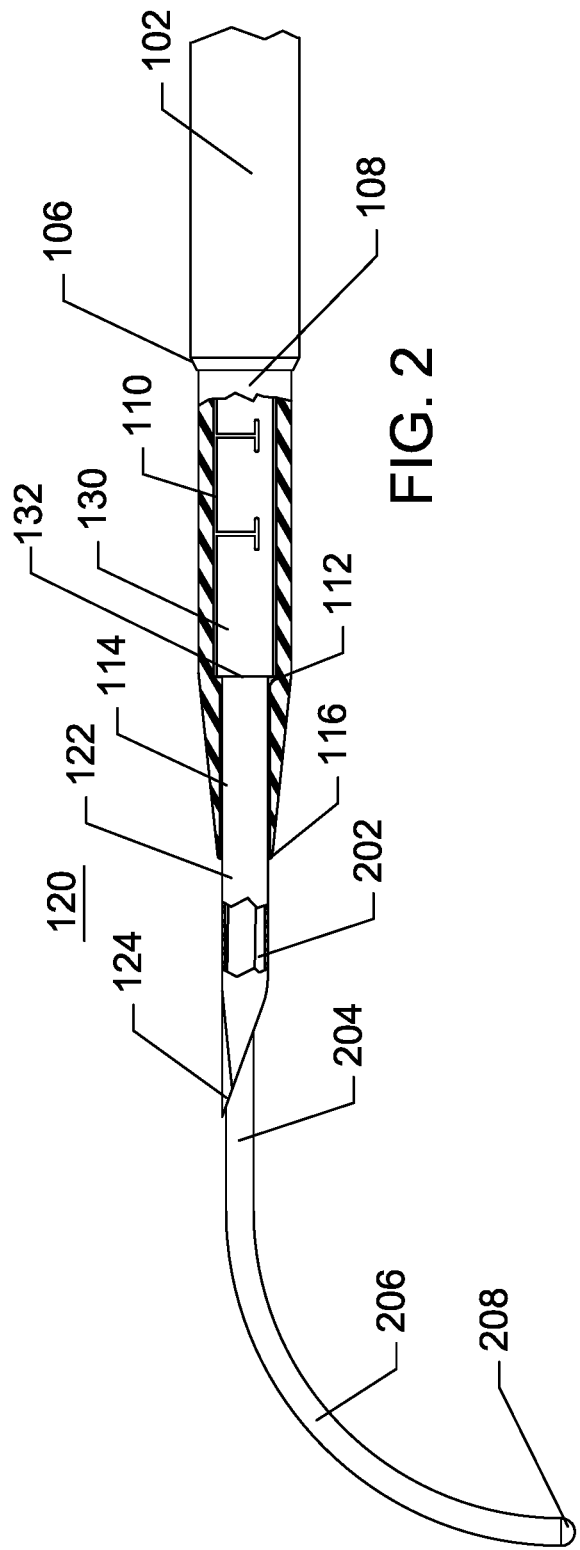
FIG. 2 illustrates the steerable endoluminal punch (steerable endoluminal punch), as viewed from the side in cross section, wherein the steerable endoluminal punch has been introduced through the introducer and a large guidewire is advanced through the central lumen of the steerable endoluminal punch, according to an embodiment of the invention.

In accordance with current terminology pertaining to medical devices, the proximal direction will be that direction on the device that is furthest from the patient and closest to the user, while the distal direction is that direction closest to the patient and furthest from the user. These directions are applied along the longitudinal axis of the device, which is generally an axially elongate structure having one or more lumens or channels extending through the proximal end to the distal end and running substantially the entire length of the device.

In an embodiment, the invention is an endoluminally, transvascularly, or endovascularly placed tissue punch, with internal deflectability or the ability to articulate, at its distal end, in a direction away from its longitudinal axis. The punch can also be termed a catheter, needle, guidewire, or cannula. The punch shaft is generally fabricated from stainless steel, nitinol, cobalt nickel alloy, or other metals and comprises an outer tube, an inner tube, a central lumen capable of accepting a guidewire, and a distal articulating region. The shaft can further comprise a polymeric coating over at least part of its exterior, at least part of its interior, or both. The deflecting or articulating mechanism is integral to the punch. The punch, needle, guidewire or catheter is sufficiently rigid, in an embodiment, that it can be used as an internal guidewire or internal guide catheter. The punch is useful for animals, including mammals and human patients and is routed through body lumens or other body structures to reach its target destination.

In an embodiment, the punch can comprise an optional removable core wire or stylet, an inner tube and an outer tube. The inner tube can comprise a sharpened distal end to facilitate tissue puncture or it can be blunted and flat or rounded. The sharpened end can comprise bevels, facets, conical tapers, sharpened blade-like structures, or the like. The core wire or stylet can be blunted at the distal end to prevent damage to structures such as tissue, the sheath, or the dilator (obturator) during advancement of the endoluminal punch, caused by the sharpened distal end of the endoluminal punch. In different embodiments, the stylet can be removable or non-removable. In some embodiments, the stylet can have a large diameter to minimize trauma and shield sharp structures on the distal tip of the endoluminal punch. The endoluminal punch further comprises a hub at its proximal end which permits grasping of the punch and can also include a stopcock or valve to serve as a lock for the stylet or other internal wire, as well as a valve for control of fluid passage into and out from the innermost lumen within which the stylet or inner core wire resides. The hub can further comprise additional ports to facilitate the administration or withdrawal of fluids or pressure measurement. The additional ports can be terminated with Luer lock connectors or with flexible lead lines terminated with Luer lock connectors, stopcocks, or the like. The proximal end further can comprise one or more control mechanisms to manipulate the amount of articulation at the distal end of the catheter. The proximal end further is terminated with a female Luer or Luer lock port, which is suitable for attachment of pressure monitoring lines, dye injection lines, vacuum lines, a combination thereof, or the like. Other structures can be provided to alter the distal tip of the endoluminal punch such as changing it from blunter and less traumatic to sharper and more capable of tissue penetration. Such distal tip altering structures can include a piercing stylet which can have a sharp distal end or which transmits energy to the distal tip of the endoluminal punch. The energy can be in the form of simple manually applied force, mechanical vibration, mechanical rotation, ultrasound energy emission, high intensity focused ultrasound, electrical power to heat the distal tip, radiofrequency energy, cryogenic energy, laser energy, and the like. The distal tip altering structure can comprise a quick release or controlled retraction mechanism which can be dumb or it can be responsive to measurements of force, tissue properties, or the like.

Other embodiments of the inventions comprise methods of use. Keeping the method of use as close to current techniques is preferable since it reduces the learning curve and physician confidence in the procedure. The general procedure comprises placing a guidewire beyond the right atrium via a percutaneous access point in the right femoral vein or jugular vein. A transseptal introducer is advanced over the guidewire, the transseptal introducer comprising a sheath and a dilator (or obturator). The dilator or obturator further comprises a shaft, a tapered distal tip, a central through lumen, and a hub affixed to the proximal end of the shaft. The sheath can comprise a hemostasis valve to seal to the dilator shaft, a side port with stopcock communicating with the central lumen of the sheath, and the like. The sheath and the dilator can comprise a pre-formed curve near the distal end. The guidewire is next removed and a transseptal needle or other crossing system is advanced through the central lumen of the dilator or obturator. In other embodiments, the guidewire can be left in place and the steerable endoluminal punch can be routed over the guidewire through the transseptal introducer or without the transseptal introducer altogether.

The transseptal needle (steerable endoluminal punch) with the transseptal introducer riding on its back can be targeted at a specific site on the interatrial septum, generally in the area of the fossa Ovalis. The tissue is tented by the dilator to stretch the tissue at the target site and exert a crossing force on the tissue. The transseptal needle is preferably retracted within the blunt distal tip of the tapered obturator/dilator to prevent any chance of unwanted or inadvertent tissue perforation. Once the target is reached, the transseptal needle is advanced distal to the distal tip of the obturator (dilator) thus exposing it to the tissue and causing cutting of the tented tissue. The transseptal needle and obturator/sheath are advanced across the tissue to gain access to the other side. The tissue must expand or split to permit the large diameter introducer dilator and sheath to pass through the incision created by the transseptal needle (steerable endoluminal punch). The transseptal needle and dilator can be removed at this time to provide a pathway through the sheath or a guidewire can be reinserted to provide a track for subsequent catheterizations.

In another embodiment, the core wire, obturator or stylet is sharpened and serves as a tissue punch. In this embodiment, the distal end of the hollow tubes of the punch are blunted and made relatively atraumatic. Once the core wire punch has completed tissue penetration, the outer tubes are advanced over the central punch wire through the penetration and into the left atrium. In another embodiment, a pressure monitoring device such as a catheter tip pressure transducer, or a pressure line terminated by a pressure transducer, can be affixed to a quick connect, generally a Luer fitting, at the proximal end of the punch hub. By monitoring pressure, it is possible to determine when the distal end of the punch has passed from, for example, the right atrium into the left atrium, because the pressure versus time curves in these two chambers are measurably, or visually, different. The proximal end of the hub further has provision for attachment to a dye injection line for use in injecting radiographic contrast media through the central lumen of the punch. Typically, a manifold can be attached to the Luer fitting on the proximal end of the hub, the manifold allowing for pressure monitoring, for example on a straight through port, and for radiopaque dye injection, for example through a side port. A stopcock, or other valve, can be used to control which port is operably connected to the central lumen of the punch.

In some embodiments, the inner tube, the outer tube, or both can have slots imparted into their walls to impart controlled degrees of flexibility. The slots can be configured as "snake cuts" to form a series of ribs with one or more spines. The spines can be oriented at a given circumferential position on the outer tube, the inner tube, or both. The spines can also have non-constant orientations. In some embodiments, only the outer tube is slotted. The slots can be generated within the distal portion of the outer tube where the curve is generated. This bendable distance can range between about 0.5-cm and 20-cm of the end and preferably between about 1-cm and 12-cm of the distal end. The slot widths can range between 0.001 inches and 0.010 inches with a preferable width of about 0.001 to 0.005 inches. In exemplary embodiments, the slot widths are about 0.003 inches. In some embodiments, it is desirable to have the outer tube bend in one direction only but not in the opposite direction and not in either lateral direction. In this embodiment, cuts can be made on one side of the outer tubing within, for example, the distal 10-cm of the tube length. Approximately 10 to 600 cuts can be generated with a width of approximately 0.001 to 0.015 inches. The cut depth, across the tube diameter from one side, can range between 0.01 and 0.9 of the tube's diameter. In an embodiment, the cut depth can be approximately 0.4 to 0.6 of the tube's diameter with a cut width of about 0.005 inches or less. A second cut can be generated on the opposite side of the tube wherein the second cut is approximately 0.005 inches or less. In an embodiment, the outer tube can be bent into an arc first and then have the slots generated such that when the tube is bent back toward the 0.005-inch wide cuts, the tube will have an approximately straight configuration even through each tube segment between the cuts is slightly arced or curved.

An energized steerable endoluminal punch system 100 and 200 configurations can be used for tissue punch, incision, or penetration, apparatus, etc. They can, in other embodiments, comprise the structure of a guidewire, a stiff track over which other devices or catheters are advanced, an introducer, a catheter, a delivery catheter for an implant or fluids, a therapeutic catheter, a diagnostic catheter, a catheter to support other procedures, or the like. The steerable endoluminal punch can be monitored using fluoroscopy and radiopaque markers affixed or integral to the steerable endoluminal punch. It can also be monitored using ultrasound guidance such as with transesophageal echocardiography (TEE), intracardiac echocardiography (ICE), real-time three-dimensional echocardiography from transducers and systems affixed to the steerable endoluminal punch.

FIG. 1A illustrates a side view, in partial breakaway, of a steerable endoluminal punch introducer 100 comprising a sheath 102 and a dilator 108. The sheath 102 comprises a sheath wall 104 further comprising an optional reinforcing structure 118 and a lumen 106. The sheath 102 further comprises a hub (not shown) which can comprise a hemostasis valve, grasping surfaces, and the like. The dilator 108 comprises a hub (not shown), a dilator wall 140, a main central lumen 110, a lumen stepdown 112, a distal lumen 114, a distal taper 142, and a distal end 116. The dilator 108 is shown inserted through the lumen 104 of the sheath 102 and protrudes out the distal 106 end of the sheath 102.

Referring to FIG. 1A, the introducer sheath 102 can be fabricated from materials such as, but limited to, polyethylene, high density polyethylene (HDPE), low density polyethylene (LDPE), polyurethane, Hytrel, Pebax, PVC, polyolefin, polyester, fluoropolymers such as PTFE, FEP, PFA, and the like. The introducer sheath 102 can further comprise a reinforcing structure 118, which can comprise a braid, a coil, or similar structures fabricated from very strong stiff elastomeric materials such as, but not limited to, stainless steel, nitinol, tungsten, cobalt nickel alloys, and the like. The introducer sheath 102 can further comprise one or more radiopaque markers near the distal end to facilitate positioning in the patient using fluoroscopic imaging, ultrasound, MRI, or the like.

The dilator 108 can be fabricated from the same materials as the sheath 102 and can also comprise one or more radiopaque markers for imaging and positioning purposes. The dilator 108, the sheath 102, or both can have their polymeric materials loaded with radiopaque contrast materials such as, but not limited to, barium, bismuth, and the like. For example, a compound of about 10% to 40% barium sulfate in HDPE is commonly used to make dilators. These items 102 and 108 can further employ lubricious coatings to facilitate reduced friction interaction with themselves and surrounding tissue. The sheath 102 distal end can also comprise electrodes (not shown) operably connected to the proximal end of the sheath 102 for the purpose of ultrasonic imaging, or tissue penetration using HIFU, Radiofrequency energy, or the like. In a preferred embodiment, the dilator 108 has an outer diameter of about 8 to 9 French. The main inner lumen 110 has a preferred diameter of about 0.080 inches and the secondary inner lumen 114 has a diameter of about 0.060 inches. The sheath 102 retains a standard internal diameter which is about 8 to 9 French and the external diameter of the sheath 102 is about 11 to 12 French, which is not different than that of current transseptal introducer systems.

FIG. 1B illustrates a side view, in partial breakaway, of a steerable endoluminal punch introducer 100 of FIG. 1A, comprising a sheath 102 and a dilator 108. In this illustration, an endoluminal punch, steerable endoluminal punch, or needle 120 has been inserted through the lumens 110 and 114 of the dilator 108 such that the distal end of the steerable endoluminal punch 120 protrudes out the distal end 116 of the dilator 108. The steerable endoluminal punch comprises an outer tube 130, having a central lumen and a distal end 132, an inner tube 122, having a central lumen 202 (not shown), and a distal end 124, which is sharpened in the illustrated embodiment. The steerable endoluminal punch distal end exterior diameter is about 0.032 to 0.070 inches with a preferred diameter of about 0.050 inches to about 0.065 inches. The steerable endoluminal punch internal lumen can be about 0.036 to about 0.062 inches. The outer tube 130 can have an outside diameter ranging from about 0.046 inches to about 0.080 inches with a preferred range of about 0.050 inches to about 0.075 inches. This steerable endoluminal punch is much larger in diameter than current transseptal needles and yet still fits within current transseptal introducer sheaths. Of course, the dilator lumen needs to be enlarged as illustrated in FIG. 1A to accept this large diameter steerable endoluminal punch.

The main advantage of a large diameter steerable endoluminal punch 120 is that it cuts a larger incision relative to the sheath size so that the sheath has an easier time penetrating tough fibrous tissue than if the incision is created with a smaller, non-energized steerable endoluminal punch. The larger incision makes it easier (lower force exerted by the user) for the introducer sheath and dilator to be inserted through the incision created by the steerable endoluminal punch. Control over the deflection of this punch 120 and the surrounding introducer, especially in steerable versions is improved because of greater off-center positioning and moment generation by a steering mechanism.

FIG. 2 illustrates a side view, in partial cross section, of the steerable endoluminal punch 120 inserted through the introducer 100, further comprising a guidewire 204 inserted through the central lumen 202 of the steerable endoluminal punch 120. The guidewire 204 further comprises an optional flexible or floppy region 206 proximate the distal end, and a rounded distal tip 208. The flexible or floppy region 206 can comprise a pigtail shape, a J-shape, a straight floppy region, or the like. The stiffness of the flexible or floppy region 206 is substantially less than that of more proximal regions of the guidewire.

Referring to FIG. 2, the guidewire 204 can be pre-inserted into the patient and the steerable endoluminal punch routed over the guidewire. In other embodiments, the guidewire 204 can be exchanged for a different guidewire initially placed in the patient. In other embodiments, the guidewire 204 can be pre-loaded into the steerable endoluminal punch prior to using the steerable endoluminal punch to puncture tissue and then be extended distally into the patient after a tissue crossing has occurred. In some embodiments, the guidewire 204 can be placed in the patient and used to route the steerable endoluminal punch into place without the use of a transseptal introducer 100. The guidewire 204 can comprise diameters of about 0.010 to about 055 inches with preferred diameters of about 0.021 inches to about 0.040 inches. Guidewire 204 length can vary depending on how long a device measures that is routed over the guidewire. It is always beneficial to have a bit of the guidewire to grasp after the device has been routed over the guidewire. Guidewires 204 can be coated with lubricious coatings such as PTFE, FEP, PFA, and the like. The guidewire 204 can serve as a stylet to protect the sharp tip of the steerable endoluminal punch 120 in other embodiments. The guidewire 204 can be used to prevent the steerable endoluminal punch from impinging on unwanted tissue after its intended crossing has occurred. The guidewire 204 can be left in the patient after the steerable endoluminal punch 120 has been removed to permit advancement of other devices into location over the guidewire 204.

Figure 3:
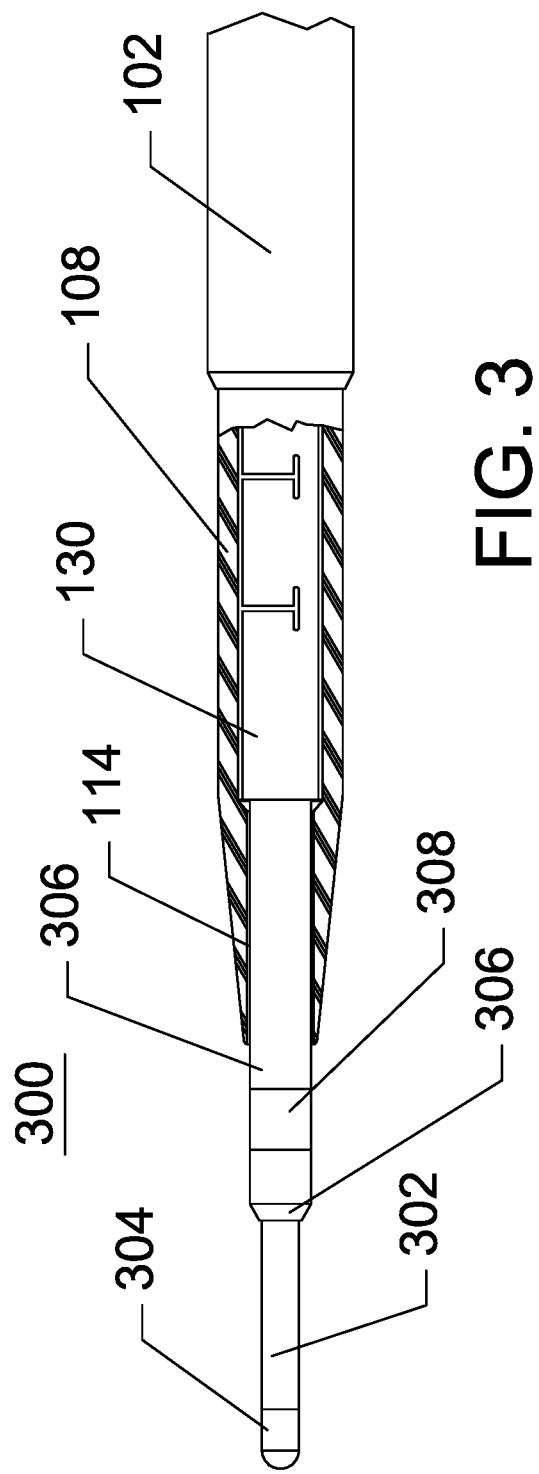
FIG. 3 illustrates a steerable endoluminal punch further comprising a guidewire wherein the guidewire comprises an RF electrode at its distal end, according to an embodiment of the invention.

FIG. 3 illustrates a steerable endoluminal punch system 300 comprising the introducer 100, the steerable endoluminal punch 300 comprising an inner tube 306 comprising a blunted (non-sharp) distal end 306, and an optional radiopaque marker 308. The steerable endoluminal punch system 300 further comprises a guidewire 302 further comprising an electrode 304 at its distal end, which can be operably connected to a power source at the proximal end of the guidewire to impart energy such as radiofrequency energy, HIFU energy, or the like, to the electrode 304. Such energy can be used to burn a hole in the tissue larger than that of the electrode 304, itself. The electrode 304 can further comprise, in part or in whole, a radiopaque structure fabricated from standard radiopaque materials such as, but not limited to, gold, platinum, platinum iridium, tungsten, and the like. This guidewire can comprise soft, flexible regions proximal to the electrode 304 and features to cause curling or sideways deflection of the guidewire after tissue penetration to render the electrode 304 inoperable.

Figure 4:
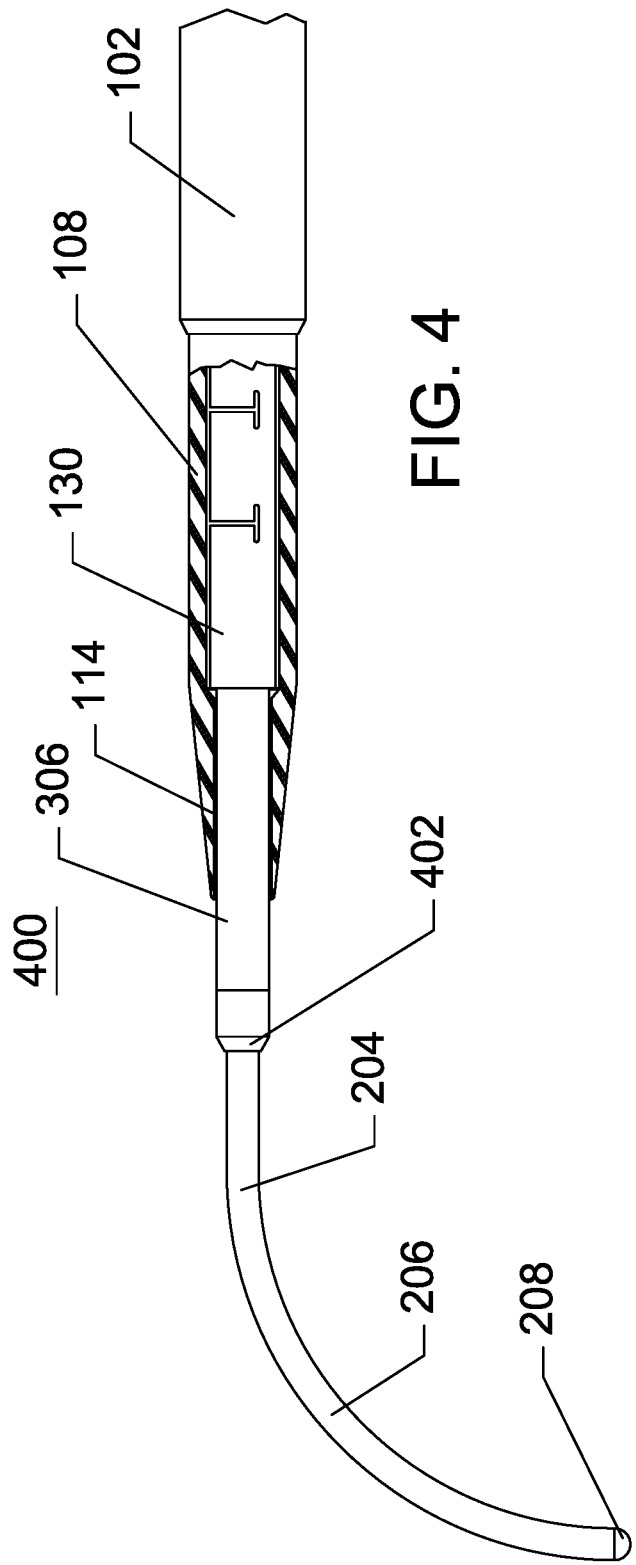
FIG. 4 illustrates a steerable endoluminal punch further comprising a RF electrode at its distal end and further capable of accepting a large diameter guidewire, according to an embodiment of the invention.

FIG. 4 illustrates, in partial cross-section, a steerable endoluminal punch system 400 comprising the introducer 100, the steerable endoluminal punch 400, comprising an inner tube 306 comprising an electrode 402 affixed to the distal end of the inner tube 306. The steerable endoluminal punch system 300 further comprises the guidewire 204 further comprising the more flexible, floppy region 206 and a rounded atraumatic distal tip 208. The electrode 402 at the distal end of the steerable endoluminal punch inner tube can be operably connected to a power source at the proximal end of the steerable endoluminal punch to impart energy such as radiofrequency energy, HIFU energy, or the like, to the electrode 402. Such energy can be used to burn a hole in the tissue larger than that of the electrode 402, itself. The electrode 402 can further comprise, in part or in whole, a radiopaque structure fabricated from standard radiopaque materials such as, but not limited to, gold, platinum, platinum iridium, tungsten, and the like. This guidewire can comprise soft, flexible regions 206 proximal to the distal end 208 and features to cause curling or sideways deflection of the guidewire after tissue penetration. This guidewire feature can reduce the chance of inadvertent tissue penetration after the intended puncture is completed.

Figure 5:
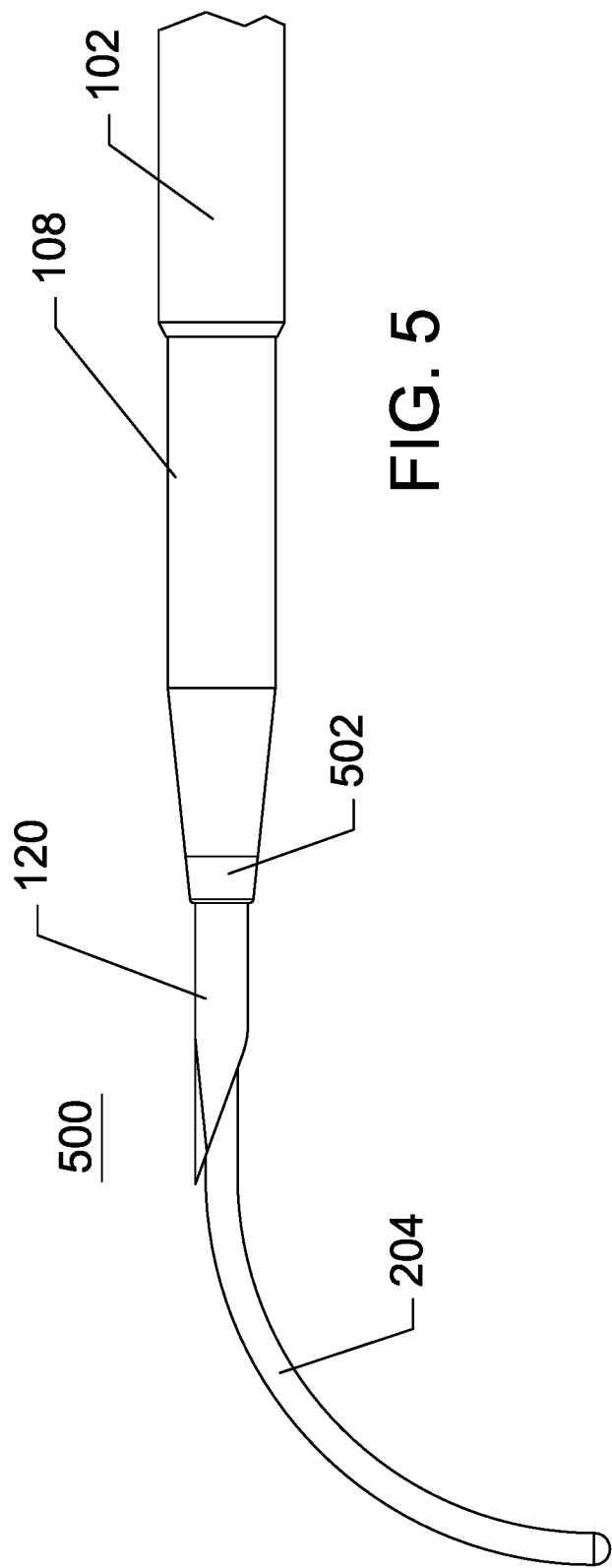
FIG. 5 illustrates a side view of a steerable endoluminal punch capable of accepting a guidewire and further wherein the punch is advanced through an introducer wherein the introducer comprises an RF electrode at its distal end, according to an embodiment of the invention.

FIG. 5 illustrates a side view of a steerable endoluminal punch system 500 comprising the steerable endoluminal punch 120 being inserted through an introducer 102 & 108 comprising an electrode 502 affixed proximate the distal end of the dilator tapered tip. The electrode 502 can be operably connected to a power source by way of an electrical bus (not shown) to a fitting (not shown) at the proximal end of the introducer. The electrode 502 can be used to impart energy such as, but not limited to radiofrequency energy, HIFU energy, and the like, to the tissue, thus enlarging the hole created by the steerable endoluminal punch. Typically energy in the range of 5 to 30 joules is appropriate for this application with a preferred range of about 10 to 20 joules. In this embodiment the steerable endoluminal punch 120 can utilize a sharp distal end to create the primary tissue incision. With use of the electrode 502, a smaller diameter steerable endoluminal punch can be used because the electrode enlarges the tissue puncture thus allowing a large dilator and introducer sheath to be passed through the incision in the tissue.

Referring to FIG. 5, the central lumen of the dilator can be of constant diameter and not comprise a step-down. Thus, a guidewire could be inserted through the central lumen of the dilator and used as a protective element for the dilator and sheath. The guidewire, of course, also serves as a routing means to guide the introducer sheath system into the target region. In this embodiment, the steerable endoluminal punch component may be eliminated and just a standard guidewire used with an introducer having an electrode at its tip. Smaller systems, employing a standard 0.035 inch diameter guidewire which fit smoothly but closely to the lumen of the introducer can be used in this embodiment. The electrode, commonly powered by an RF generator can be a ring electrode or just located on one circumferential location on the tip of the dilator.

Figure 6A:
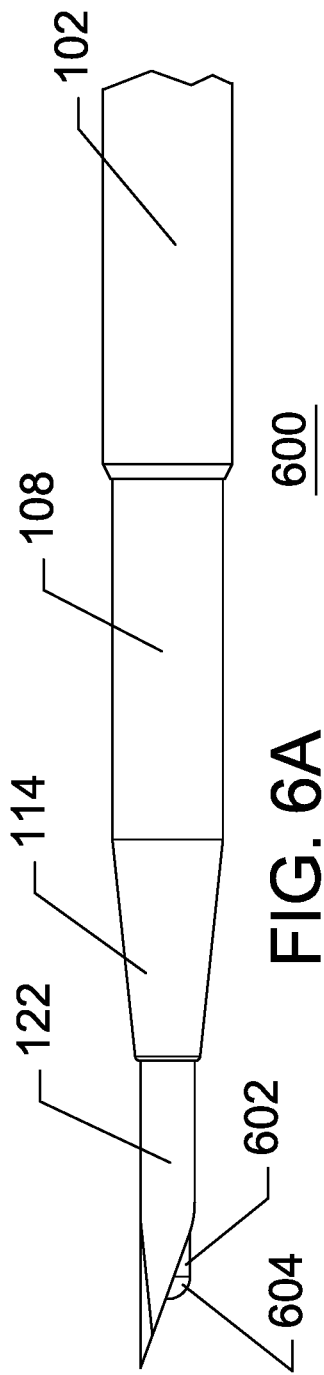
FIG. 6A illustrates a steerable endoluminal punch inserted through the central lumen of a introducer dilator wherein a protective stylet, or guidewire, is retracted and armed, according to an embodiment of the invention.

FIG. 6A illustrates a steerable endoluminal punch system 600 comprising the steerable endoluminal punch of FIG. 1B. A stylet 602 having an atraumatic tip 604 is inserted into the lumen of the steerable endoluminal punch 600. The stylet 602 is configured with a mechanism similar to that used in safety trocars to pre-load the stylet 602. The stylet 602, in some embodiments, can comprise a spring-loaded actuator preferably in the hub of the stylet, which is affixed to the hub of the steerable endoluminal punch. The spring can comprise a very low spring force, sufficient to advance the stylet 602 out the distal end of the steerable endoluminal punch inner tube 122 but insufficient to advance the stylet 602 when encountering tissue. Thus, the stylet 602 is being forced back into the steerable endoluminal punch lumen by the tissue, which has not yet been crossed.

Figure 6B:
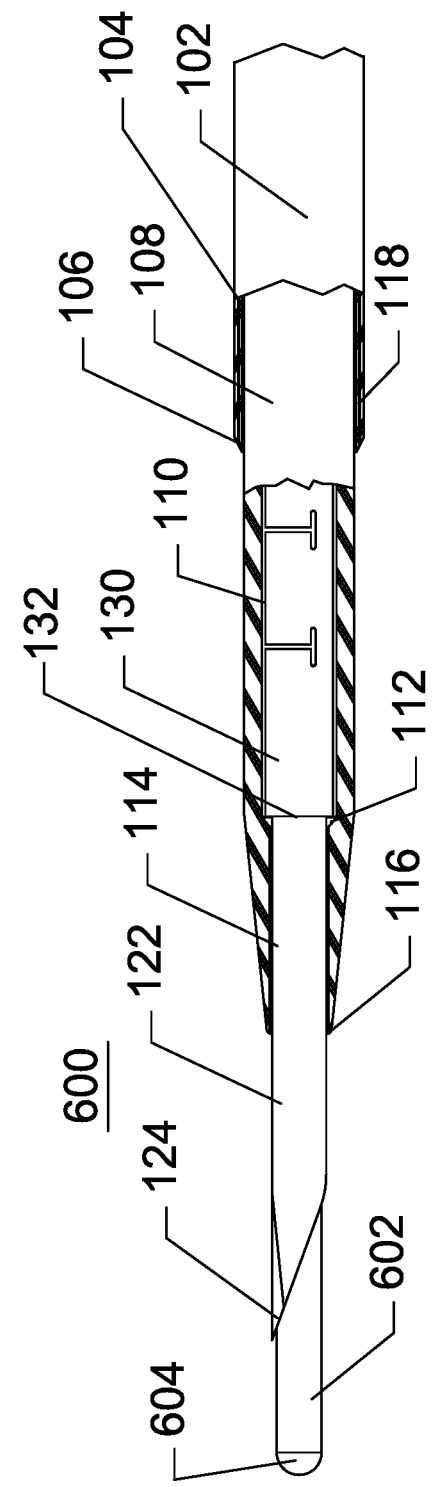
FIG. 6B illustrates the steerable endoluminal punch of FIG. 6A wherein the protective stylet, or guidewire. has been actuated and has advanced to a position which is distal to sharp distal end of the endoluminal punch in a random, uncontrolled manner so that the blunt distal end of the protective stylet serves to shield the sharp distal end of the endoluminal punch from inadvertently puncturing unplanned tissue or other structures, according to an embodiment of the invention.

FIG. 6B illustrates the steerable endoluminal punch system 600 wherein the stylet 602 has been advanced out the distal end of the steerable endoluminal punch by force generated by the user, a spring, a magnet, an electromagnetic actuator, or the like. The system is configured such that after the compression force on the introducer is relieved because the introducer, stylet 602 or the steerable endoluminal punch distal end has passed through the tissue. Once through the tissue, the stylet 602 is forced distally by a weak spring (not shown), preferably operably affixed within the hub (not shown) of the stylet 602, to protect the sharp tip 124 from further incisions. Once fully advanced, the stylet 602 can be set to re-lock, thus preventing the blunt end from retracting proximally to the sharp end 124 of the steerable endoluminal punch. These systems can include a safety which is released such that any change in force triggers a spring to advance the stylet 602 distally relative to the steerable endoluminal punch, thus enabling a protective shield. In some embodiments, the stylet 602 can be a guidewire. The guidewire or stylet 602 can further comprise steering mechanisms such as the one described herein so that once left behind, the stylet or guidewire can be used to precisely guide other devices into place and forcefully hold curves, etc.

Figure 7:
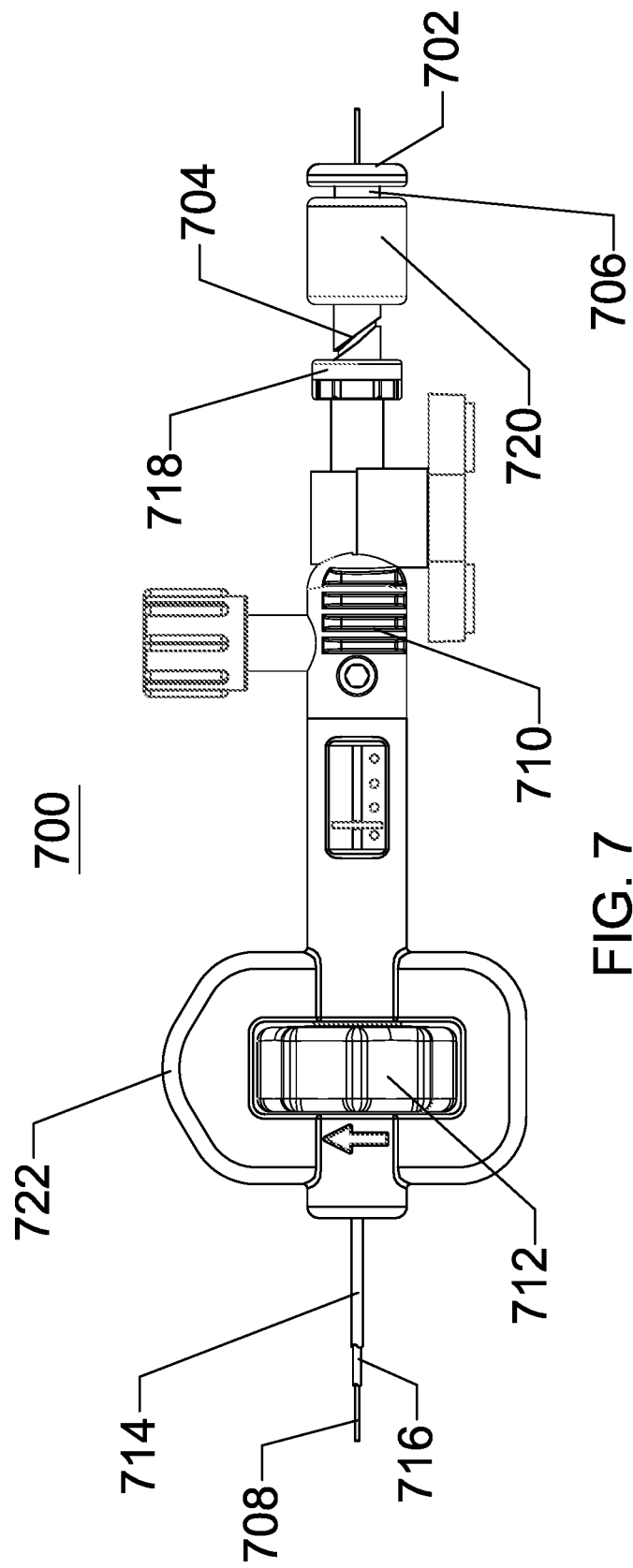
FIG. 7 illustrates the hub end of an endoluminal punch wherein a guidewire controller is releasably affixed to the hub, according to an embodiment of the invention.

FIG. 7 illustrates the proximal hub end of a steerable endoluminal punch 700, comprising a guidewire controller 720 releasably affixed to a steerable endoluminal punch hub 710 and further comprising a guidewire grasping knob 702, a Luer lock fitting 718, a guidewire motion control system 704, a guidewire 708, a knob support 722, an outer tube 714, and an inner tube 716.

Referring to FIG. 7, the guidewire 708 is temporarily grasped by the guidewire lock 702. The guidewire 708 is biased distally by a spring (not shown) within the guidewire controller 720. The spring (not shown) force is lightly applied so that the sharp tip pushes through the tissue, which restrains the guidewire. The spring then moves distally when the tip of the steerable endoluminal punch has finally crossed tissue and the guidewire is free to advance because it is not restrained by tissue. The guidewire 708 then advances by spring bias and can, in some embodiments, lock in a position at a limit point where it protrudes distally to the distal end of the steerable endoluminal punch. The lock can be deactivated by a mechanism on the guidewire controller to reset the guidewire, remove the guidewire, or whatever.

By this methodology, the guidewire 708 can be used as a safety to protrude out and shield the sharp tip of the steerable endoluminal punch from being able to penetrate tissue inadvertently after the initial crossing. The guidewire 708 can then be unlocked from the controller 720 so that it be routed appropriately and the steerable endoluminal punch removed from the patient.

FIG. 8A illustrates a steerable endoluminal punch system 800 comprising an endoluminal punch 120, a dilator 108, an introducer sheath 102, an electrode 502, and a guidewire 804.

Referring to FIG. 8A, the guidewire 804 can comprise a floppy tip or pre-set curve, as illustrated to form a J-tip, U-tip, or other configuration. This curved tip can serve to shield the sharp point of the steerable endoluminal punch from causing tissue damage if inadvertently advanced too far, for example. The dilator 108 comprises a tapered distal end that facilitates incision enlargement after initial creation by the steerable endoluminal punch. The sheath 102 follows the dilator across the tissue and serves as the route through which diagnostic or therapeutic procedures are conducted. This guidewire, item 804, can be the same guidewire as item 708 of FIG. 7 or it can be a different guidewire. The guidewire 804 can comprise a sharp tip, a blunt, atraumatic tip, as illustrated, or it can comprise a powered electrode for RF, cryogenic, ultrasound or other energy source transmission, reception, or both. The electrode 502 can be a ring electrode, as illustrated, or it can be a line or point electrode. The electrode 502, which is affixed to the tip of the dilator 108, can be operably connected to an electrocautery unit by way of an electrical bus, not shown, connecting to the proximal end of the dilator.

FIG. 8B illustrates a axial view in cross-section of the dilator tube 108 comprising a tube body 806, a central lumen 808, and an electrical bus 810 which comprises one or more wires 814. The electrical bus 810 can be fabricated by use of a multi-lumen extrusion and placement of a wire into a small lumen 812. In other embodiments, a wire or wires 814 can be insert molded into the extrusion. The central lumen 808 is configured to allow passage of instruments including, but not limited to, a transseptal needle, as described herein. The wires 814 in the electrical bus 810 can comprise materials such as, but not limited to, stainless steel, copper, silver, and the like.

Figure 9A:
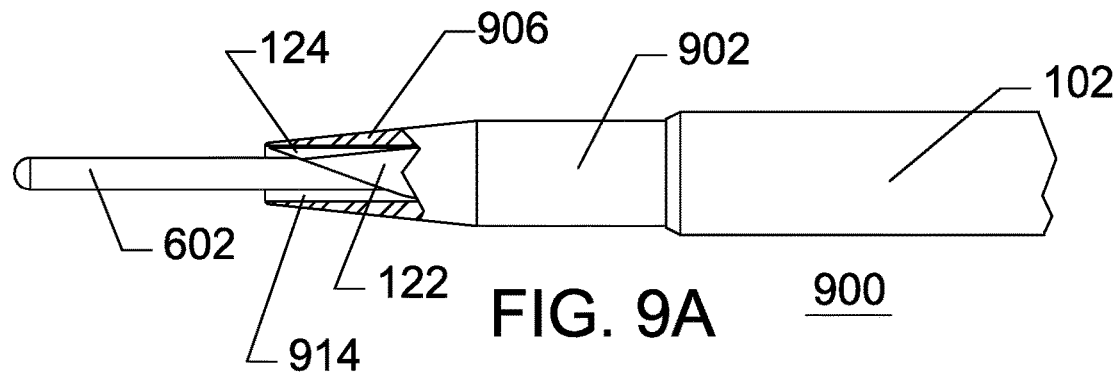
FIG. 9A illustrates a side view, with the dilator in partial breakaway, of a steerable endoluminal punch distal end comprising a punch tip that is retracted within the lumen of a dilator and a guidewire inserted through the central lumen of the punch, according to an embodiment of the invention.

FIG. 9A illustrates the distal end, in partial breakaway side view, of a steerable endoluminal punch system 900 comprising an inner tube 122 having a sharp distal end 124 integrated within an introducer sheath 102 by way of a dilator 902 further comprising a tapered distal end 906 and further comprising a guidewire 602. The dilator 902 can be affixed to the steerable endoluminal punch or it can be slidably disposed to move axially relative to the steerable endoluminal punch, as illustrated herein.

The distal end 124 of the steerable endoluminal punch is shown retracted within the distal end of the dilator 902. The guidewire 602, which is slidably movable relative to the inner tube 122, projects distally to the distal end 124 of the steerable endoluminal punch inner tube 122. The dilator 902 is configured with an outside diameter which fits closely with the inside diameter of the sheath 102 while sliding smoothly for easy translation controlled by a user at the proximal end (not shown). The dilator 902 comprises a lumen 914 that is configured to fit with the outside diameters of the inner tube 122, the outer tube 130, or both and can be a sliding fit, a press fit, a bond, or a weld. The dilator 902 can be fabricated from polymeric materials such as polyethylene, HDPE, LDPE, polyimide, PEEK, PEBAX, Hytrel, stainless steel, tantalum, cobalt nickel alloy, nitinol, and the like. The dilator 902 can be affixed to the inner tube 122, an outer tube 130 (not shown), or both. The dilator 902 serves to space the inner tube 122 within the sheath and prevent any scraping, cutting, skiving, or other interaction by the distal end 124 with the outer tube 102.

Figure 9B:
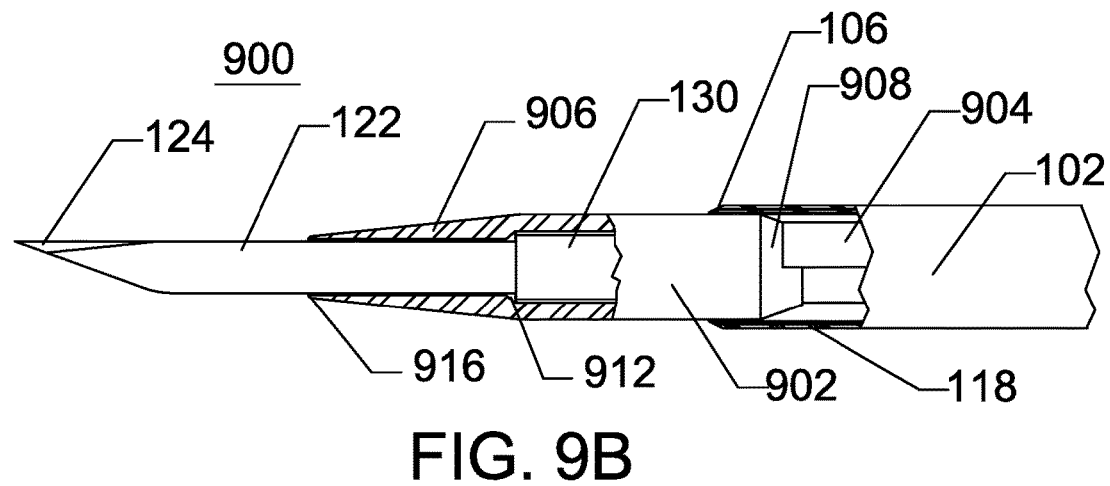
FIG. 9B illustrates a side view, with the dilator and introducer sheath in partial breakaway, of a steerable endoluminal punch wherein the dilator has been retracted (or conversely, the steerable endoluminal punch advanced) to expose the sharp distal end of the steerable endoluminal punch and further wherein the dilator is a bulb shaped configuration that mates the outside diameter of the steerable endoluminal punch to the inside diameter of the introducer sheath, according to an embodiment of the invention.

FIG. 9B illustrates the steerable endoluminal punch system 900 in partial breakaway wherein the distal end of the steerable endoluminal punch 124 has been advanced distal to the distal end 916 of the dilator 902. Additional detail of the system 900 is illustrated. The steerable endoluminal punch system 900 comprises the sheath 102 further comprising a sheath wall 118, a sheath distal end 106, the dilator 902, the dilator lumen 914, a dilator lumen stepdown 912, the outer tube 130, a dilator proximal diameter reduction or taper 908, and a dilator control rod or linkage 904.

The dilator control rod or linkage 904 can be affixed to the proximal end of the dilator 902, typically in the region of the proximal dilator taper 908. The dilator control rod or linkage 904 can be a tube, it can be a partial tube (or another functional cross-section) such as a half-pipe as illustrated, it can be a rod of pretty much any functional cross-section. The dilator control linkage 904 preferably comprises both compression and tension functions suitable to move the dilator 902 axially forward or backward relative to the inner tube 122. The dilator control linkage 904 can also be configured to torque and rotate the dilator 902 relative to the inner tube 122, the outer tube 130, or both. The dilator control rod 904 can be eliminated if the dilator 902 is permanently axially affixed to the inner tube 122, the outer tube 130, or both. The dilator control linkage 904 can comprise composite material construction such as a polymeric tube with a braid or coil reinforcement fabricated from metals or high strength plastics like PET or polyimide.

At least one advantage of this system 900 is that the steerable endoluminal punch can be adapted to an introducer sheath without the need for a separate dilator. The steerable endoluminal punch system, then, just requires the steerable endoluminal punch itself and an introducer sheath without the need for a separate dilator since the dilator 902 is integrated with the steerable endoluminal punch. The dilator 902 can further comprise one or a plurality of lumens, channels, or fenestrations (not shown) that operably permit fluid flow to pass axially down the annulus between the sheath 102 and the steerable endoluminal punch outer tube 130 and reach the distal end of the introducer sheath without the need to remove the steerable endoluminal punch or the dilator.

In practice, the steerable endoluminal punch can be preloaded within the introducer sheath 102 and be routed, atraumatically, into the patient with or without the need for the guidewire 602 since the sharp distal end 124 can be recessed or retracted within the dilator 902. The steerable endoluminal punch can be used to perform tissue crossing and the guidewire 602 can be left in place while the steerable endoluminal punch, the sheath 102, or both are removed from the patient, all in a single step. The steerable endoluminal punch dilator 902 can be configured as a safety device to force retraction of the steerable endoluminal punch inside the dilator or forward motion of the dilator relative to the distal end of the steerable endoluminal punch, in either case the purpose being to cover the tip of the steerable endoluminal punch so as to render it atraumatic.

In other embodiments, a guidewire can be routed through a percutaneous access or cutdown to a vessel or body lumen and transited to a location proximate a treatment or target site. A steerable endoluminal punch is next routed over the guidewire to the location of the treatment or target site. The guidewire can be withdrawn. The guidewire can next be clamped into a system that advances the guidewire under spring or magnetic force against tissue to be crossed. The Sharp end of the steerable endoluminal punch can advance across the tissue thus resulting in the guidewire being forced backward against the spring or magnetic force and retracted into the tip of the steerable endoluminal punch so as to maintain a sharp penetrating distal end to the steerable endoluminal punch. The steerable endoluminal punch then penetrates the tissue and once the central lumen of the steerable endoluminal punch has cleared the tissue, the guidewire is advanced under spring, electromagnetic, or magnetic force to form a protective blunt structure protruding from the distal end of the steerable endoluminal punch. A dilator and introducer sheath can be next advanced across the tissue. If extra help is needed to increase the size of the incision through the tissue, a blade, a cutting edge, a fin blade, or an energy radiating electrode can be disposed on or about the surface of the dilator tip to increase the size of the initial incision for passage of a larger diameter introducer sheath. The steerable endoluminal punch, the dilator with electrode, or both, can comprise a wiring harness or cable with optional plug emerging that is operatively connected to the electrode or steerable endoluminal punch tip. The wiring harness can be plugged or operationally connected to a Radio Frequency (RF) power source, High Intensity Focused Ultrasound (HIFU) power source, or the like.

Figure 9C:
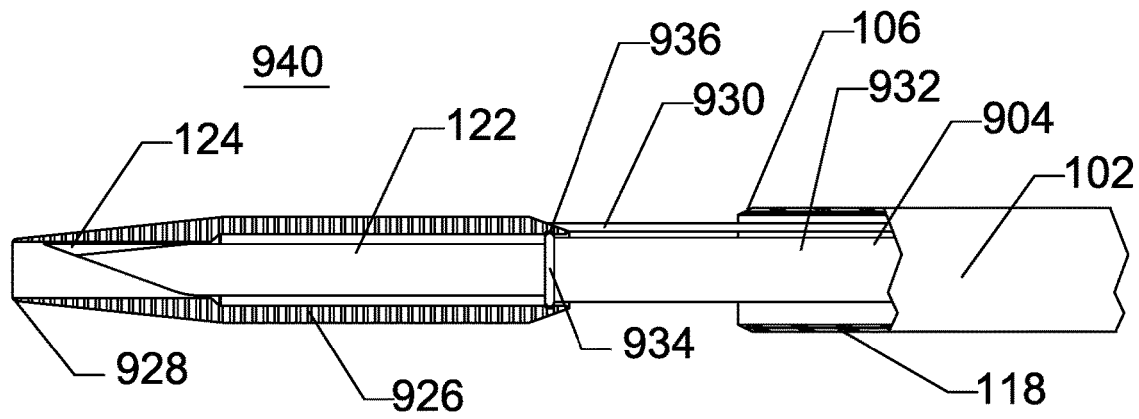
FIG. 9C illustrates a side view, in partial cross-section and breakaway of a steerable endoluminal punch and introducer system wherein the dilator portion of the introducer is actually a component of the steerable endoluminal punch, rather than the introducer, according to an embodiment of the invention.

FIG. 9C illustrates a side view, in partial breakaway and cross-section of a steerable endoluminal punch comprising an integral dilator which is routed through a separate introducer sheath 102 further comprising the sheath wall 118 and the distal end 106. The steerable endoluminal punch 940 comprises an outer tube 932 further comprising a releasable catch 934 affixed or integral to the distal tip of the outer tube 932. The steerable endoluminal punch further comprises the inner tube 122 further comprising the sharp or otherwise tissue piercing distal tip 124, a bulbous dilator 926 further comprising an atraumatic distal tip 928, a detent 936 and an optional push rod 930. The system 940 may comprise a spring or other linear actuator system (not shown).

Referring to FIG. 9C, the push rod 930 can comprise a rod having both column strength and tensile strength, it can also comprise torqueability and the ability to rotate thus causing linear motion of the dilator tip 926 using a jackscrew type system. The push rod 930 can allow for the dilator tip 926 to be advanced distally to a reset or initial condition on the steerable endoluminal punch after being locked, loaded, and fired a first time. This reset can occur by an action on the part of the user applied at the proximal end of the steerable endoluminal punch or introducer or it can occur through more automated mechanism. The push rod 930 can, in other embodiments, comprise a tubular structure that can surround the outer tube 932 of the steerable endoluminal punch 940.

In operation, the steerable endoluminal punch with integral dilator 940 protects the sharp tip 124 from inadvertently piercing tissue or components of the introducer sheath 102.

The integral dilator 940 is lightly snapped to the outer tube by means of the detent 936 and catch 934. When the steerable endoluminal punch is pressed against tissue, the integral dilator 940 is forced proximally by the tissue and the steerable endoluminal punch sharp tip 124 then pierces the tissue. Once through the tissue, the sharp tip 124, the inner tube 122, and the dilator 926, which has moved proximally until it hits a stop (not shown). At this point, the dilator 926 advances under force, through the tissue, as does the sheath 102. The spring or actuator (not shown) can be set to automatically advance, or reset, the dilator 926 back over the sharp tip 124.

Figure 10A:
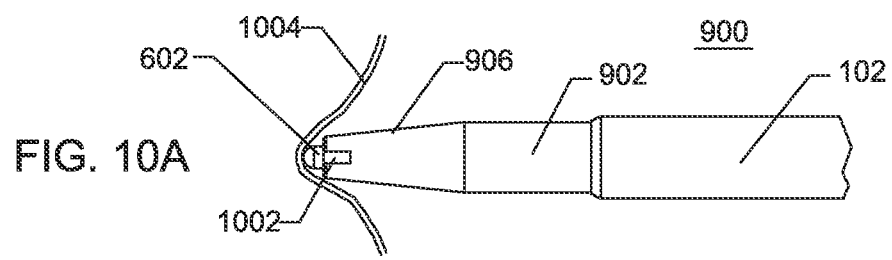
FIG. 10A illustrates a steerable endoluminal punch system having an introducer, a dilator, and a retracting guidewire or protective shield, pressed up against tissue but not piercing, or incising, the tissue, according to an embodiment of the invention.

FIG. 10A illustrates a side view of a steerable endoluminal punch introducer and steerable endoluminal punch 900 being advanced against biological tissue 1004. The introducer and steerable endoluminal punch 900 comprises the sheath 102, the dilator 902 further comprising a tapered dilator tip 906, a blunt stylet or guidewire 602 and an optional energy emitting electrode 1002. The tissue 1004 can include, but is not limited to, interatrial septum, interventricular septum, liver tissue, lung tissue, kidney tissue, and the like. The stylet 602 can be armed with a magnetic or electromagnetic actuator and be triggered by changes in capacitance as the tip of the steerable endoluminal punch passes through tissue. The blunt stylet 602 can also comprise an RF electrode at its tip, which is operably connected to a RF power supply at the proximal end of the stylet. The blunt stylet can then be used to perforate tissue without the need for a sharp edge on the steerable endoluminal punch. The system can be guided by a real-time 3-D ultrasound system for precise positioning and targeting.

Figure 10B:
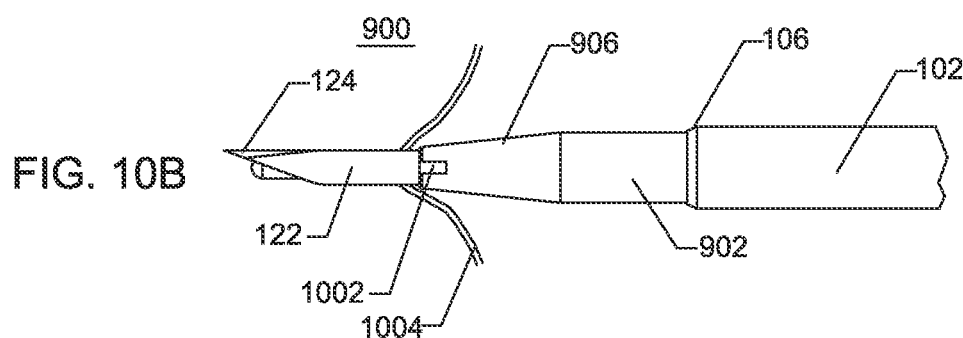
FIG. 10B illustrates; a steerable endoluminal punch wherein the distal end of the steerable endoluminal punch, which is sharp has penetrated the tissue, but the dilator and sheath have not penetrated through the incision, according to an embodiment of the invention.

FIG. 10B illustrates a side view of the steerable endoluminal punch and introducer 900 with the steerable endoluminal punch sharp distal tip 124 of the steerable endoluminal punch inner tube 122, protruding out past the distal end of the dilator 902. The steerable endoluminal punch has penetrated the tissue 1004 but the tapered end of the dilator 906 has not yet penetrated the tissue. The stylet or guidewire 602 has also crossed through the tissue 1004 but is still retracted within the inner tube 122 and does not prevent the function of the sharp distal tip 124 in making a tissue incision. The sharp distal end 124 of the steerable endoluminal punch can, in other embodiments, comprise an RF electrode, HIFU electrode, or other energy emitting transducer. The sharp distal end 124 can, in other embodiments, comprise a blunted, flat or rounded distal end in configuration, especially when combined with the energy emitting transducer (not shown). Once the sharp distal end 124 has crossed the tissue, the guidewire or stylet 602 advances distally under controlled mechanisms such as, but not limited to, spring bias, linear actuator, fluid pressure, or the like. Such control mechanism can be operationally connected to the guidewire 602, the sharp end 124, the dilator tip 906, or the like, and be physically located in a hub or other apparatus affixed at the proximal end of the introducer and steerable endoluminal punch 900. The electrode or energy emitting transducer 1002 on the dilator tapered end has not yet been activated and thus, the dilator 902 has not opened and crossed through the incision 1006 in the tissue 1004.

Figure 10C:
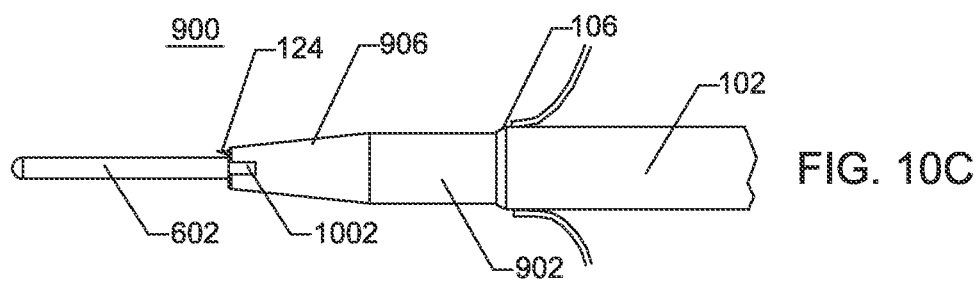
FIG. 10C illustrates A steerable endoluminal punch wherein the dilator and sheath have now penetrated through the tissue, either through dilation or through additional cutting by an RF electrode while the guidewire has sprung forward to serve as a shield for the sharp tip, according to an embodiment of the invention.

FIG. 10C illustrates a side view of the steerable endoluminal punch and introducer 900 wherein the sheath 102 has just passed through the incision and the stylet or guidewire 602 has advanced beyond the sharp distal end 124 of the inner tube 122 and the sharp distal end 124 is now retracted (just a tiny bit of the tip 124 is showing) within the blunt distal end of the dilator taper 906.

Figure 10D:
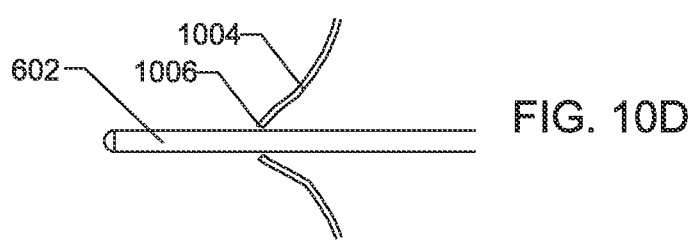
FIG. 10D illustrates the guidewire remaining through the tissue incision, after removal of the steerable endoluminal punch, according to an embodiment of the invention.

FIG. 10D illustrates a guidewire 602 or stylet left behind following removal of the steerable endoluminal punch and introducer 900. The guidewire 602 remains placed through the incision 1006 in the tissue 1004. The guidewire 602 is preferably pre-curved or floppy, or both, at a location proximate the distal end, so that it deflects laterally following release into a body cavity beyond the tissue 1004. The guidewire 602 preferably has a diameter ranging from about 0.018 inches to about 0.050 inches with a preferred range of about 0.021 inches to 0.038 inches. The guidewire 602, especially in larger diameter versions, can be used as a pathway to guide follow-on devices into place. Such devices include, but are not limited to, heart valves, valve leaflet clips, atrial appendage occluders, annuloplasty rings, papillary muscle repair mechanisms, RF or cryotherapy devices, and the like.

FIG. 11A illustrates a side view of the distal end of a steerable endoluminal punch 1100, in partial breakaway, comprising an outer tube 1102, an inner tube 1104 further comprising a sharp distal tip 1106 a central lumen 1130, a side wall fenestration 1110, a seal weld 1108 between the inner tube 1104 and the outer tube 1102, a vent hole 1114, an inflation channel 1112, an outer polymeric sleeve 1124, a dilatation balloon 1116, a balloon internal volume 1118, a proximal balloon bond 1120, and a distal balloon bond 1122.

FIG. 11B illustrates a side view of the steerable endoluminal punch 1100 being retracted into an introducer sheath 102 and dilator 1126, further comprising a distal taper 1128. The volume 1118 is typically pressurized with non-compressible fluid such as water, saline, or the like. The fluid filling the volume 1118 is being evacuated through the inflation channel 1112, and the balloon 1116 is being refolded down into a low-profile configuration. The refolding of the balloon 1116 material can be facilitated by setting the balloon material into pleats or wings that assume a spiral galaxy arm-type shape to minimize the profile of the collapsed material for easiest withdrawal. The balloon 1116 can comprise materials such as, but not limited to, polyimide, polyester, PET, latex rubber, silicone rubber, or the like. The balloon 1116 can be formed using methods such as, but not limited to, stretch blow molding. The outer polymeric sleeve 1124 is suitable to prevent escape or ingress of fluids through the sidewall of the steerable endoluminal punch but it can also serve as a base structure onto which the balloon 1116 bonds 1120, for example, can adhere, bond, seal, etc.

A guidewire 804 is also shown having been inserted through the central lumen 1130 of the inner tube 1104. In this case, the guidewire 804 comprises a flexible or floppy distal end which allows it to curl or coil after exiting the distal end of the inner tube lumen 1130. The guidewire 804 can comprise exposed metallic components or an electrode 1132 at its distal end. The electrode or exposed metallic components 1132 can be operably connected to a power source such as, but not limited to, a radiofrequency generator, an ohmic heating power supply, a HIFU generator, or the like. The guidewire 804 can comprise a central lumen (not shown) and can further be steerable using the same mechanisms as the steerable endoluminal punch. The central lumen (not shown) of the guidewire 804 can communicate through to the environment through side windows, an end opening, or the like.

Figure 12A:
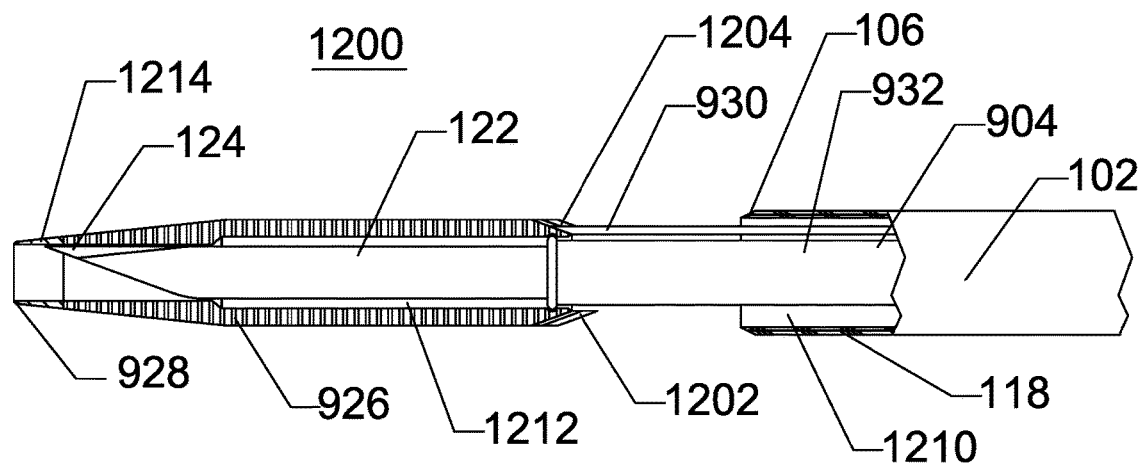
FIG. 12A illustrates a steerable endoluminal punch comprising a movable solid dilator further comprising proximally facing cutting blades which can be withdrawn against tissue to create a radially oriented incision larger than that of the steerable endoluminal punch is capable of making on its own, according to an embodiment of the invention.

FIG. 12A illustrates a side view of the distal end of a steerable endoluminal punch 1200, in partial breakaway and cross-section, comprising an introducer sheath 102 further comprising a wall 118, a distal end 106, and a central lumen 1210. The steerable endoluminal punch 1200 also comprises a dilator 926. The dilator 926 comprises a bulbous structure tapering to a distal end 928, a lumen 1212 sized to slidably move axially over the inner tube 122 and outer tube 932, a proximal bulb end 1204, and a dilator pusher or control linkage 930. The dilator 926 further comprises the inner tube 122 further comprising the lumen 1130 (see FIG. 11A and FIG. 11B). The dilator 926 can optionally comprise one or more cutting blades 1202 and 1204, which can be used to assist with incision enlargement during retraction of the dilator 926 back inside the sheath 102.

In practice the dilator 926 is advanced distally beyond the distal end 106 of the sheath 102 to cross a tissue layer. The tissue collapses around the shaft 932. Upon withdrawal of the dilator 926 back into the lumen 1210 of the sheath 102, the blades 1202 and 1204 can cut tissue to increase the size of the incision. Note that the needle tip 124 is retracted inside the dilator 124 at this point in the procedure.

Figure 12B:
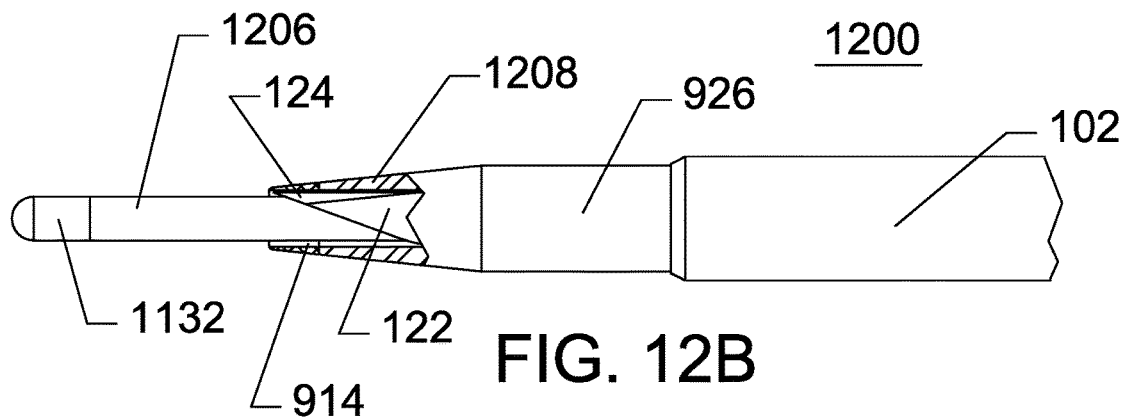
FIG. 12B illustrates the steerable endoluminal punch of FIG. 12A during insertion or removal from the patient, wherein a large diameter stylet protrudes past the distal end of the steerable endoluminal punch, further wherein the dilator provides a shield against the sharp edge 124 to prevent the sharp edge from inadvertently puncturing tissue or skiving plastic, according to an embodiment of the invention.

FIG. 12B illustrates the steerable endoluminal punch 1200 of FIG. 12A wherein the dilator 926 has been retracted within the lumen 1210 of the sheath 102. The needle tip 124 remains retracted inside the protection of the dilator 926. A guidewire or protective stylet 1206 is shown protruding beyond the steerable endoluminal punch tip 124. The tapered part of the dilator 1208 is shown in cross section. The stylet 1206 or guidewire can be locked in place to be advanced to its illustrated position but upon release of a safety lock at the hub proximal end of the steerable endoluminal punch, a spring is capable of biasing the stylet 1206 distally but able to retract proximal to the sharp point 124 upon pressing against tissue. Once through the tissue, the stylet can spring forward and re-lock or curve to prevent inadvertent traumatic damage by the needle tip 124. The stylet 1206 can comprise a distal end that is relatively stiff, or the distal end can be floppy and deflect sideways, bending, or curling, after passing out of the lumen of the inner tube 932.

The stylet 1206 can be configured with a distal electrode or exposed wire to allow for energy delivery to the tissue to facilitate crossing. Such energy delivery can include but is not limited to, RF energy, HIFU, mechanical motion, vibration, cryogenics, ohmic heating, or the like. Alternatively, or in addition to, the energy radiating stylet 1206, the introducer dilator 1208 can comprise an electrode or other energy delivery device 1214, affixed at or near the distal end of the dilator 1208 taper. The dilator tip electrode 1214 can receive power which is operably transmitted through the dilator pusher or control rod 930 or the power can be transmitted through the inner tube 904 by way of a power source affixed to the proximal end of the steerable endoluminal punch 1200.

This steerable endoluminal punch system works for cutting holes in tissue such as blood vessels, organs, muscle, or other, but it can also be used for biopsy systems, embolic material or device injection, thrombolysis material injection, clot removal systems, marker placement, implant placement, diagnostics, endoscopic use, ultrasound delivery, and the like. The steerable endoluminal punch can also comprise a catheter having a blunt end, rather than being a cutting or piercing instrument. The steerable endoluminal punch can comprise a guidewire, an introducer sheath, a guide catheter, or the like.

The steerable endoluminal punch may be used in a method of crossing the septum of the heart, to gain access to the left atrium through the right atrium, in which the steerable endoluminal punch steerable endoluminal punch is advanced over a guidewire. The guidewire is first inserted into the vascular, and the distal tip of the guidewire is located in the right atrium. The steerable endoluminal punch is then advanced over the guidewire, into the superior vena cava. The guidewire is now positioned so that the distal tip of the guidewire rides within the distal tip of the steerable endoluminal punch, and both reside in the superior vena cava, proximate the right atrium.

The surgeon then operates the steerable endoluminal punch to steer the distal end of the punch to place the distal end of the punch against the interatrial septum (preferably at the fossa ovalis). Once the desired position of the SEP distal tip is confirmed the steerable endoluminal punch and guidewire are pressed against the interatrial septum/fossa ovalis so as to tent or dimple the interatrial septum/fossa ovalis. Continued advancement of the SEP is now halted and the position of the distal end of the SEP is now maintained by the user or by some built in position guard. At this point, any guards or safeties are withdrawn or disabled and the SEP passes through the interatrial septal tissue by virtue of the elastic stretching of the tip of the SEP against the interatrial septal tissue.

The distal tip of the punch is then advanced distally until the sharp distal tip of the punch perforates the interatrial septum/fossa ovalis The distal end of the punch, along with the guidewire, and the surrounding introducer are then advanced into the left atrium of the heart.

The surgeon delivers an introducer sheath and dilator over the steerable endoluminal punch. Preferably the introducer is 18F, 34 F, or larger, replacing the now standard 8.5F introducer, so that only one introducer need be used.

The surgeon then withdraws the punch but leaves the guide wire in place, with the distal end of the guidewire remaining within the left atrium. The punch may be withdrawn entirely from the body at this point, or remain in place to accommodate insertion of a large bore introducer.

The surgeon may then advance a large bore introducer sheath or a large bore guide catheter over the guidewire. This entire procedure can be completed quickly without the need for device exchanges because all functions including tissue crossing, guidewire placement, and guide catheter placement have already been completed using a single device comprised by nested instruments.

In this method, the surgeon need not exchange this first introducer for a larger bore introducer, so that at least one catheter exchange step is avoided. Thus, without exchanging the large bore introducer for a different introducer, with the guidewire remaining in place, the surgeon may deliver a device delivery catheter, diagnostic catheter, therapeutic catheter through the introducer sheath and into the left atrium.

In other embodiments of the methods, an implant or surgical repair device can be introduced to the left atrium of the heart. A guidewire is advanced into the right atrium of the heart. The guidewire can be steerable or non-steerable. A large bore introducer sheath with integral dilator can be advanced over the guidewire. A SEP can optionally be passed over the guidewire and inside the lumen of the dilator of the large bore introducer sheath and over the guidewire. The large bore introducer sheath can replace the TSI of the prior discussion. Using this methodology, the transseptal introducer (TSI) is not necessary as an intermediate step. The large bore introducer sheath can comprise cutting elements or electrodes to facilitate tissue passage should fibrous scar tissue or very floppy tissue be encountered while crossing. The large bore introducer sheath is advanced into the left atrium of the heart over the SEP or other crossing device. The SEP or other crossing device can be removed leaving behind the large bore introducer sheath, guidewire, or both.

In yet another embodiment, a steerable guide catheter can be advanced over the initially placed guidewire (steerable or not). The steerable guide catheter has a large diameter and is initially not different than the large bore introducer sheath described earlier. In this embodiment, however, following removal of the SEP, a large bore introducer sheath can be advanced through the lumen of the steerable guide catheter. The steerable guide catheter can be constructed so as to have very thin walls and powerful steering control. The steerable guide catheter can now be articulated to hold a specific arc or bend at a specific location that does not vary while the large bore introducer sheath is being manipulated (advanced, withdrawn, rotated, etc.) within the heart. The large bore introducer sheath can, of course be similarly steerable so that multiple degrees of steering, as well as multiple stable locations of steering are enabled. The large bore introducer sheath can now be used to deploy an implant, device, therapy, or diagnostic. This type of double catheter system becomes advantageous using construction methodology described herein since the walls of the guide catheter and introducer sheath, as well as the SEP and SGW can all be rendered extremely thin while still maintaining strength and steerability.

In another method embodiment, any of the systems described herein can be inserted into a patient using a superior approach (e.g. jugular vein, etc.) rather than the inferior approach (femoral vein or artery) described in previous sections. Due to the inherent steerability of the system, lateral positioning is facilitated by the SEP and its introducer sheath system. Once the SEP and the introducer sheath (TSI, guidewire, large bore introducer, guide catheter, or a combination thereof) are located within the left atrium of the heart, the system can be straightened out so that very little curvature is required. Following removal of the SEP a large bore introducer can be used to approach the mitral valve, for example with little or no curvature. This is important because a valve implant, when compressed diametrically for implantation, becomes a long, stiff structure that does not turn corners well. The implant can be navigated through the large bore introducer sheath and directly to the mitral valve annulus so as to facilitate implantations of valves, annuloplasty rings, tissue commissure clips, chordae repair systems, and the like. This superior approach method is even more useful when approaching the tricuspid valve, which would be a very tight bend using an inferior approach.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

What is claimed is:

1. A method of crossing the interatrial septum of a patient's heart, to gain access to the left atrium through the right atrium, in which a steerable endoluminal punch is advanced over a guidewire, said method comprising the steps of:
    inserting the guidewire into vasculature of the patient to locate the distal tip of the guidewire in the superior vena cava;
    advancing the steerable endoluminal punch over the guidewire to locate the distal end of the steerable endoluminal punch in the right atrium, such that the distal tip of the guidewire is disposed within the distal tip of the steerable endoluminal punch, and both reside in the right atrium;
    operating the steerable endoluminal punch to steer the distal end of the punch to place the distal end of the punch against the interatrial septum;
    pressing the punch and guidewire distal tips against the interatrial septum to tent the interatrial septum;
    advancing the distal tip of the punch and guidewire distally until a sharp distal tip of the punch perforates the interatrial septum;
    delivering a large bore introducer sheath and a dilator over the steerable endoluminal punch, to locate a distal end of the large bore introducer sheath in the left atrium;
    without exchanging the large bore introducer sheath for a different introducer sheath, with the guidewire remaining in place, removing the steerable endoluminal punch and delivering a device delivery catheter, diagnostic catheter, or therapeutic catheter through the large bore introducer sheath and into the left atrium.

2. The method of claim 1, wherein the large bore introducer sheath is 18F or larger.

3. The method of claim 1, further comprising the step of:
    after the punch perforates the interatrial septum, advancing the distal tip of the guidewire into the left atrium.

* * * * *